United States Patent [19]

Schwartzman et al.

[11] Patent Number: 4,579,945

[45] Date of Patent: Apr. 1, 1986

[54] PURIFICATION OF TREHALOSE DIMYCOLATES

[75] Inventors: Steven M. Schwartzman, Stevensville; Edgar E. Ribi, Hamilton, both of Mont.

[73] Assignee: Ribi ImmunoChem Research, Inc., Hamilton, Mont.

[21] Appl. No.: 587,841

[22] Filed: Mar. 12, 1984

Related U.S. Application Data

[63] Continuation of Ser. No. 372,843, Apr. 29, 1982, abandoned.

[51] Int. Cl.$^4$ ............................................. C07H 1/06
[52] U.S. Cl. ............................................. 336/127; 536/119
[58] Field of Search ............... 536/1.1, 119, 124, 127; 424/180

[56] References Cited

U.S. PATENT DOCUMENTS 4,307,229  12/1981  Liav et al. ........................ 424/180
4,340,588  7/1982   Woodard ........................... 424/180

Primary Examiner—Johnnie R. Brown
Assistant Examiner—Elli Peselev
Attorney, Agent, or Firm—Burgess, Ryan & Wayne

[57] ABSTRACT

A method of purifying crude trehalose dimycolates (TDM) is disclosed which comprises dissolving crude TDM in a solvent and then subjecting said solution to a low pressure silica gel column operating at a pressure between about 10 and 300 psi wherein the silica gel comprises particles in the range of between about 15 and 63 microns. The product of this process is also disclosed.

6 Claims, No Drawings

PURIFICATION OF TREHALOSE DIMYCOLATES

This application is a continuation of application Ser. No. 372,843, filed 4/29/82, now abandoned.

BACKGROUND OF THE INVENTION

The subject matter of the present invention is directed to a method of purifying crude trehalose dimycolates (TDM). TDM is an isolate of bacteria and when combined with cell wall skeleton (CWS) forms a composition which is effective in obtaining suppression and regression of tumor cells.

The combination of cell wall skeleton and TDM is known in the art (See Biologically Active Components from Mycobacterial Cell Walls. II. Suppression and Regression of Strain-2 Guinea Pig Hepatoma; Meyer, et al, *Journal of the National Cancer Institute*, Volume 52, No. 1, January, 1974; and Mycobacterial Cell Wall Components in Tumor Suppression and Regresssion; Ribi, et al, *National Cancer Institute Monograph* No. 39, pages 115-120, October, 1972.

Cell wall skeleton is essentially cell wall which has had much of the protein and lipids normally found in the cell wall removed. It is a polymeric mycolic acid arabinogalactan mucopeptide containing remnants of trehalose mycolates ("P3") and undigested tuberculoproteins. Cell wall skeleton is obtained from any mycobacteria including, but limited to, *M. smegmatis, M. phlei, Nocardia rubra, Nocardia asteroides, Corynebacterium diphtheriae, Corynebacterium parvum, M. kansasii, M. tuberculosis* (Strain H 37 RV and Ayoma B), and *M. bovis* Strain BCG. Additionally, cell wall skeleton may be obtained from such non-mycobacteria as *E. coli, B. abortus* and *Coxiella burnettii*.

The process of producing cell wall skeleton is time consuming. The bacteria such as *M. bovis*, Strain BCG (bacillus Calmette-Guerin) is grown and harvested. The resulting whole cell residue is processed through a cell fractionator [Ribi Cell Fractionator (Sorvall, Model RF-1)] which disrupts the cells separating the outer envelope or cell wall from the protoplasmic impurities. The resulting cell walls are then subjected to a series of solvent extractions and enzymatic treatments (e.g., trypsin and/or chymotrypsin) to give purified cell wall skeleton.

The second component trehalose dimycolates (TDM) may be obtained from any mycobacteria including, for example, *M. avium, M. phlei, M. tuberculosis* (Strain H 37 RV and Ayoma B), *M. bovis* BCG, *M. smegmatis, M. kansasii, Nocardia rubra, M. bovinis* and *Corynebacterium diphtheriae*.

Bacteria, such as *M. avium*, are grown, harvested and then heat killed. The cell mass is extracted with several solvents and then an active, solvent-soluble fraction is extracted. This extract is further purified by a series of solvent extractions to provide crude TDM (See Biologically Active Components from Mycobacterial Cell Walls. I. Isolation and Composition of Cell Wall Skeleton and Component P3; Azuma, et al, *Journal of the National Cancer Institute*, Volume 52, pages 95-101, 1974). As disclosed in Azuma, et al, crude TDM may then be further purified by centrifugal microparticulate silica gel chromatography to give purified TDM.

CWS and TDM produced as described above can be used as an oil droplet emulsion to obtain an anti-tumor composition suitable for injection (See Immunotherapy with Non-viable Microbial Components; Ribi, et al; Annals of the New York *Academy of Science*, Volume 227, pages 228-238, Sept. 20, 1976).

The prior art emulsions, however, suffer from a major disadvantage. Impurities remaining in the purified TDM seriously affect the potency of the composition limiting its effectiveness in treating tumors. Prior art attempts at further purifying TDM have generally involved repeated time consuming costly elutions through high pressure silica gel columns. Applicants have discovered that the use of a low pressure (i.e., between about 10 and 300 psi) column with silica gel particles having a size between about 15 and 63 microns surprisingly and effectively removes virtually all impurities from crude TDM.

It is therefore an object of the invention to provide a process for purifying crude TDM. It is another object of the invention to provide a purified TDM product which can be combined with CWS to produce an oil in saline emulsion which is effective as an anti-tumor agent.

THE INVENTION

The present invention is directed to a process for purifying TDM to eliminate virtually all impurities normally associated with crude TDM. The process comprises dissolving the crude TDM in a solvent and then subjecting the solution to a low pressure silica gel column having a particle size of between about 15 and 63 microns. The pressure employed in the column is normally between about 10 and 300 psi, preferably between about 30 and 80 psi.

A wide variety of non-polar solvents may be used to dissolve the crude TDM. The preferred solvents include, for example, chloroform, ether, hexane, methanol, ethanol, tetrahydrofuran, petroleum ether, heptane, methylene chloride, ligroin, propanol, butanol, ethyl acetate, benzene, toluene, acetic acid and the like including combinations thereof.

Fractions of the purified TDM are combined and the solvent removed. The resulting product has virtually no detectable impurities (i.e., purity equal to or greater than 99.9 percent). By employing the process described above, a highly pure TDM product is obtained without the need for repetitious purifying steps. The product can be effectively combined with CWS in a conventional manner to produce a potent anti-tumor composition.

The following examples are for illustrative purposes only and are not intended to limit or in any way redefine the invention as claimed in the claims appended hereto.

EXAMPLE 1

Preparation of Crude TDM 600 g (moist weight) of whole cells of *M. phlei* which had previously been heat killed were stirred overnight on a magnetic stirrer in 4 liters of 95 percent ethanol and then vacuum filtered through a 27 cm Buchner funnel, fitted with a 24.0 cm Whatman No. 1 filter paper, into a 2 liter filter flask. The ethanol solution was removed. The cell residue was resuspended in a 2 liter flask with 1500 ml of a 1:1 ethyl ether-ethanol solution and stirred overnight on a magnetic stirrer and then filtered as described above. The ether-ethanol solution was removed and a second ethyl ether-ethanol extraction and filtration was then performed. After removal of the ether-ethanol solution, the cell residue was resuspended in 1500 ml of a 2:1 chloroform-methanol solution and stirred overnight on a magnetic stirrer and filtered through a Buchner funnel or centrifuged at 10,000 rpm for 30 seconds. The chloroform-methanol solution was removed and the extraction and filtration process repeated twice. The cell residue was air dried and bottled. The three chloroform-methanol solutions were combined and evaporated on a Buchi Roto-vapor in a tared round bottom flask. The weight of the chloroform-methanol residue was 13.0 g.

The residue was dissolved in 500 ml of a 2:1 chloroform-methanol solution and stirred for 1 hour on a magnetic stirrer and then filtered through a sintered glass Buchner funnel (coarse, 300 ml). The solvent was evaporated on a Buchi Roto-vapor in a tared round bottom flask to provide a residue weighing 12.5 grams.

The resulting residue was resuspended in 400 ml of ethyl ether and stirred on a magnetic stirrer for 1 hour. The suspension was then centrifuged in 2 screw-cap centrifuge bottles in a GSA Rotor at 5000 rpm for 30 minutes. The ether soluble fraction was then decanted. Both the ether soluble and ether insoluble fractions were preserved.

The ether insoluble material was dissolved in a 200 ml 2:1 chloroform-methanol solution and filtered through a Buchner funnel.

The ether soluble fraction was evaporated on a Buchi Roto-vapor in a tared round bottom flask and an ether soluble residue was obtained. This residue was dissolved in 300 ml of ether and precipitated into 900 ml of methanol. The precipitate was filtered through a Buchner funnel using Whatman No. 1 filter paper and combined with the 2:1 chloroform-methanol solution containing the ether insoluble material described above. The resulting solution was evaporated on a Buchi Roto-vapor in a tared round bottom flask to obtain 6.5 grams of a residue.

The residue was dissolved in 200 ml of a 2:1 chloroform-methanol solution and poured into a 500 ml separatory funnel. This solution was then added dropwise into a 2 liter flask, on a magnetic stirrer, containing 600 ml of acetone. The resulting precipitate was filtered into a Buchner funnel, air dried and placed in a tared bottle to obtain 4.5 g of crude TDM.

EXAMPLE 2

Purification of Crude TDM 2 grams of crude TDM as obtained in Example 1 were dissolved in 2 ml of a 10:1 chloroform-methanol solution and then drawn onto a 5 ml sample loop. The remainder of the loop was filled with solvent. The solution was pumped onto a silica gel 60 column (25×1000 mm) having a particle size of from about 15 to 63 microns, using an Isco Model 132 pump. The column was eluted with 800 ml of chloroform, followed by 1200 ml of a 98:2 chloroform-methanol solution at a rate of 4 ml/minute. (The flow rate is critical as it has been found that resolution is less when the flow rate is unduly increased. Consequently, elution is generally affected at a flow rate varying between about 0.1 ml to 20 mls./minute and normally at a rate between about 2 and 5 mls./minute.) The effluent from the column was then connected to a fraction collector and fractions of 8 ml per tube were collected while the column was being eluted with 3500 ml of a 96:4 chloroform-methanol solution. The tubes containing purified TDM were determined by spotting aliquots of the various fractions on TLC plates (silica gel F-254, 5×10 cm, 0.25 mm thick) using a 10:1 chloroform-methanol solution as an eluant and comparing these fractions with pure TDM previously isolated. Visualization of TLC plates were produced by spraying plates with 10 percent (w/v) of phosphomolybdic acid in ethanol. Fractions containing purified TDM were combined and solvent evaporated on a Buchi Roto-vapor in a tared round bottom flask. 358 mg of purified TDM were obtained.

What we claim is:

1. In a process for purifying crude trehalose dimycolates comprising dissolving crude trehalose dimycolates in a solvent selected from the group consisting of chloroform, ether, hexane, ethanol, methanol, tetrahydrofuran, petroleum ether, heptane, methylene chloride, ligroin, propanol, butanol, ethyl acetate, benzene, toluene, acetic acid and combinations thereof, and treating the solution to remove impurities, the improvement comprising subjecting the solution to a low pressure silica gel column at a pressure between about 10 and 300 psi and having a particle size of between about 15 and 63 microns.

2. The process of claim 1, wherein said pressure is between about 30 and 80 psi.

3. The process of claim 1, wherein said trehalose dimycolates are obtained from mycobacteria.

4. The process of claim 3 wherein the mycobacteria are selected from the group consisting of *M. avium, M. phlei, M. tuberculosis* (Strain H 37 RV and Ayoma B), *M. bovis,* BCG, *M. smegmatis, M. kansasii, Nocardia rubra, M. bovinis,* and *Corynebacterium diphtheriae.*

5. The process of claim 1 wherein elution is conducted at a rate varying between about 0.1 ml. to 20 mls./minute.

6. The process of claim 5 wherein elution is conducted at a rate varying between about 2 and 5 mls./minute.

* * * * *